US00PP21744P2

(12) United States Plant Patent
Yencho et al.

(10) Patent No.: US PP21,744 P2
(45) Date of Patent: Mar. 1, 2011

(54) SWEETPOTATO PLANT NAMED 'NCORNSP-012EMLC'

(50) Latin Name: ***Ipomoea batatas* (L.) Lam.**
Varietal Denomination: NCORNSP-012EMLC

(75) Inventors: G. Craig Yencho, Raleigh, NC (US); Kenneth V. Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/590,474

(22) Filed: Nov. 9, 2009

(51) Int. Cl.
*A01H 5/00* (2006.01)

(52) U.S. Cl. ..... Plt./258

(58) Field of Classification Search ..... Plt./258, Plt./373, 395
See application file for complete search history.

*Primary Examiner*—Annette H Para
(74) *Attorney, Agent, or Firm*—Jondle & Associates, P.C.

(57) ABSTRACT

'NCORNSP-012EMLC' is a new and distinct variety of ornamental sweetpotato having a compact, semi-upright, mounding and spreading habit; produces many short shoots; has foliage that is very deeply-lobed and light green to chartreuse colored; is highly branched and has good vigor; has distinctive twisting and outwardly curved petioles, causing the leaves to be presented on a horizontal plane; flower production is rare even under short day conditions; and is suitable for use as a landscape or containerized plant.

3 Drawing Sheets

Latin name of the genus and species: *Ipomoea batatas* (L.) Lam.

Variety denomination: 'NCORNSP-012EMLC'.

BACKGROUND OF THE INVENTION

*Ipomoea batatas* is a member of the morning glory family *Convolvulaceae*. The cultivated members of *Ipomoea batatas* are commonly produced for consumption of their enlarged storage roots and they are commonly referred to as the white or yellow sweetpotato and the orange yam. The plants of the edible sweetpotato types are typically fast-growing, green vines possessing a wide variety of leaf shapes ranging from palmate and deeply lobed, to cordate or triangular shaped leaves with no lobes. Ornamental sweetpotatoes, which have been bred and selected for their unique foliage colors, leaf shapes, and plant habits, typically do not produce large fleshy storage roots like the sweetpotato cultivated for consumption. The storage roots produced by ornamental sweetpotatoes are typically not as large because no selection has been exercised for yield, thus storage roots do not begin to swell until very late in the season and those that are produced are not very attractive.

Like their cultivated forms, ornamental sweetpotato plants are a heat loving, drought tolerant vines grown as an annual, but they possess unique foliage colors, leaf shapes, and growth habits, which have significant value in the ornamental marketplace. They are highly desirable in the landscape and ornamental industries because their foliage comes in a wide variety of colors and shapes. Also, they can be grown in a potted plant and/or mixed planting format, and they have the ability to cover a large space or hang over walls and pots creating brightly colored and textured backdrops in gardens and patios. Most ornamental sweetpotatoes grow and last the entire growing season and they require little maintenance. Moreover, these plants have few insect or disease problems.

Until the release of the Sweet Caroline series of ornamental sweetpotatoes (see below) there were six popular types of ornamental sweetpotatoes, cultivated primarily as annual, summer vines in landscaping applications. These six cultivars are: 'Blackie' (unpatented), having purple foliage and lavender flowers; 'Terrace Lime' (unpatented) and 'Margarita' (unpatented; also known as 'Sulfur'), which have large brilliant chartreuse leaves and lavender blooms; 'Black Heart' (unpatented; also known as 'Ace of Spades'), having heart-shaped leaves with burgundy purple color; 'Tricolor' (unpatented; also known as 'Pink Frost'), a variegated plant having pale green, white, and pink-margined leaves; and 'Lady Fingers' (unpatented), which has medium green, dainty leaves divided into long, thin, finger-like lobes which are complemented by burgundy stems and veins.

To meet the growing horticultural demand for ornamental sweetpotatoes it is desirable to produce new cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

'NCORNSP-012EMLC' was bred to meet the increasing demand for new ornamental sweetpotatoes. 'NCORNSP-012EMLC' is a compact, semi-upright; mounding, spreading variety producing many short shoots. This variety is distinguishable from other varieties by its very deeply-lobed light green to chartreuse colored leaves and its compact, highly branched plant habit. The plant has good vigor and distinctive twisting and outwardly curved petioles, causing leaves to be presented on a horizontal plane. The production of flowers by 'NCORNSP-012EMLC' is rare even under short day conditions. In greenhouse and field trials conducted since 2005 by the breeding program and industry collaborators 'NCORNSP-012EMLC' has been shown to be much less vigorous than *Ipomoea batatas* 'Margarita' and 'Blackie' and is suitable for use as a landscape or containerized plant.

'NCORNSP-012EMLC' originated from a conventional cross between the proprietary *Ipomoea batatas* cultivar 'NC2591-002ORN' (the female parent; unpatented) and the proprietary *Ipomoea batatas* cultivar 'NC2279-001ORN'

(the male parent; unpatented) conducted during October 2004 to April 2005 in a greenhouse in North Carolina. Botanical seed of the 'NC2591-002ORN'×'NC2279-001ORN' cross were planted in the greenhouses in North Carolina in Spring 2005. The first cycle of selection on this family was exercised in the seedling trays and survivors were transferred to a single 6-inch pot, which was then maintained in the greenhouse. Cuttings (2 each) were taken from the plants in April and planted at greenhouses in North Carolina as 2-plant un-replicated plots during late June to early July 2005. The single, individual clone now known as 'NCORNSP-012EMLC' was selected on Sep. 1, 2005 because of its combination of exceptional ornamental sweetpotato features, and has been propagated asexually since that time.

Since its selection, 'NCORNSP-012EMLC' has been asexually reproduced in greenhouses in North Carolina predominantly by vegetative propagation of vine cuttings. Successively, there have been five cycles of vegetative propagation, one cycle of tissue culture micro propagation and multiple vegetative propagation cycles to increase the plant population. Asexual reproduction of 'NCORNSP-012EMLC' by vine cuttings has shown that the unique features of the new cultivar are stable and the plant reproduces true to type in successive generations of asexual reproduction.

REFERENCE TO PLANT BREEDERS RIGHTS

Plant Breeders Rights for 'NCORNSP-012EMLC' has been applied for in Canada in October 2009. 'NCORNSP-012EMLC' has not been made publicly available or sold more than one year prior to the date of this application.

SUMMARY OF THE INVENTION

'NCORNSP-012EMLC' is a compact, semi-upright; mounding, spreading variety producing many short shoots. This variety is distinguishable from other varieties by its very deeply-lobed light green to chartreuse colored leaves and its compact, highly branched plant habit. The plant has good vigor and distinctive twisting and outwardly curved petioles, causing leaves to be presented on a horizontal plane. The production of flowers by 'NCORNSP-012EMLC' is rare even under short day conditions. The variety is much less vigorous than *Ipomoea batatas* 'Margarita' and 'Blackie' and is suitable for use as a landscape or containerized plant.

BRIEF DESCRIPTION OF THE PHOTOGRAPHS

The photographs in the drawings were made using conventional techniques and show the colors as true as reasonably possible by conventional photography. Colors in the photographs may differ slightly from the color values cited in the detailed botanical description, which accurately describe the colors of 'NCORNSP-012EMLC'. Photos were taken in summer 2009 in North Carolina, under natural light.

DETAILED DESCRIPTION OF THE NEW VARIETY

The following is a detailed description of the botanical characteristics of the new and distinct variety of *Ipomoea batatas* plant known by the variety name 'NCORNSP-012EMLC'. All colors cited herein refer to The Royal Horticultural Society Colour Chart designations (The Royal Horticultural Society, London, 1995, $4^{th}$ ed.) except where general terms of ordinary dictionary significance are used. Where dimensions, sizes, colors, and other characteristics are given, it is to be understood that such characteristics are approximations or averages set forth as accurately as practicable.

The descriptions reported herein are from 68-day-old specimens grown individually in six-inch "azalea" pots. Plant histories were taken in June 2009. 'NCORNSP-012EMLC' has not been observed under all possible environmental conditions; therefore, the phenotype may vary under different environmental conditions such as season, temperature, light intensity, day length, cultural conditions, and the like, without however any variance in the genotype.

Classification:

*Botanical name.*—*Ipomoea batatas* (L.) Lam.

*Common name.*—Sweetpotato.

*Variety name.*—'NCORNSP-012EMLC'.

Growth conditions: 'NCORNSP-012EMLC' has excellent vigor, a rapid growth rate, and is very adaptable to container culture. In locales with mild winter conditions, 'NCORNSP-012EMLC' will grow perennially; otherwise it is an annual plant. Similar to cultivated sweetpotatoes, wind or rain rarely causes much damage to 'NCORNSP-012EMLC', but if damage does occur, the plant drops the damaged leaves and grows new shoots at nodes where the leaves were lost. Under low light levels in a greenhouse, 'NCORNSP-012EMLC' can develop intumescence, which will remain on the affected foliage, but will be outgrown with new foliage.

Figure 1:
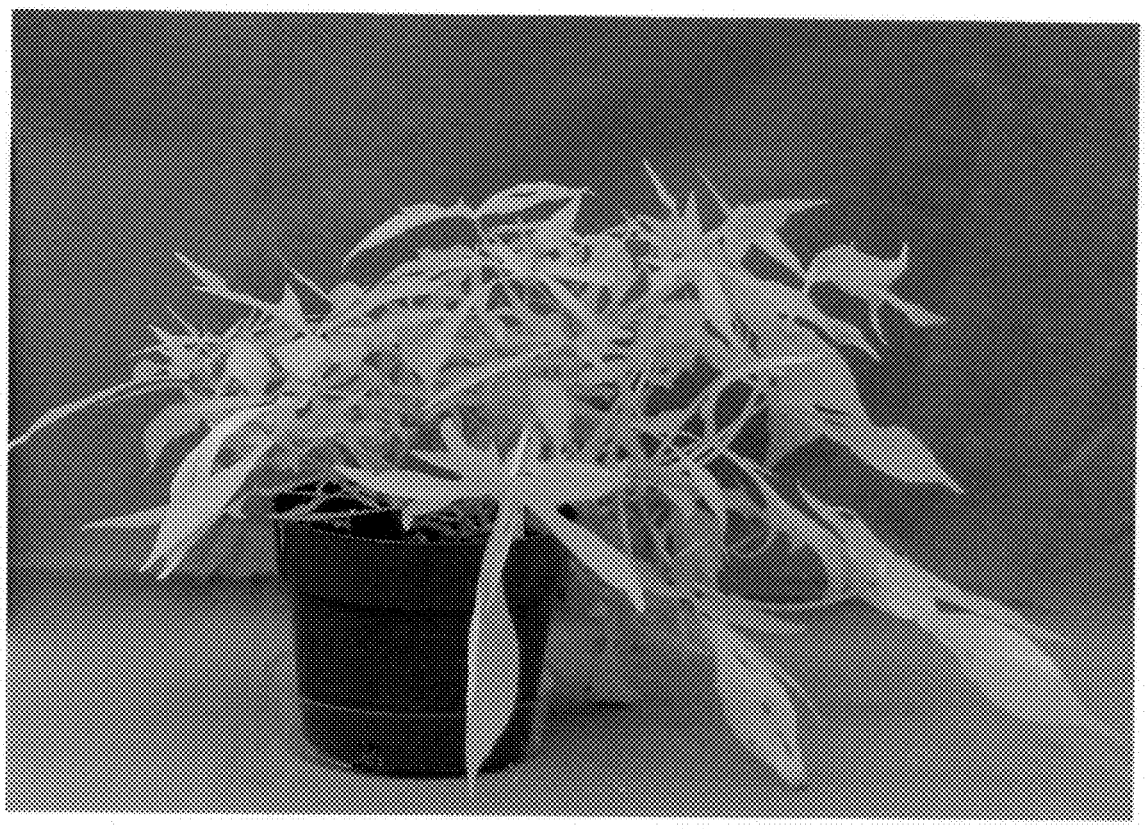
FIG. 1 shows a typical specimen of 'NCORNSP-012EMLC' from the side, 81 days after planting.
Figure 2:
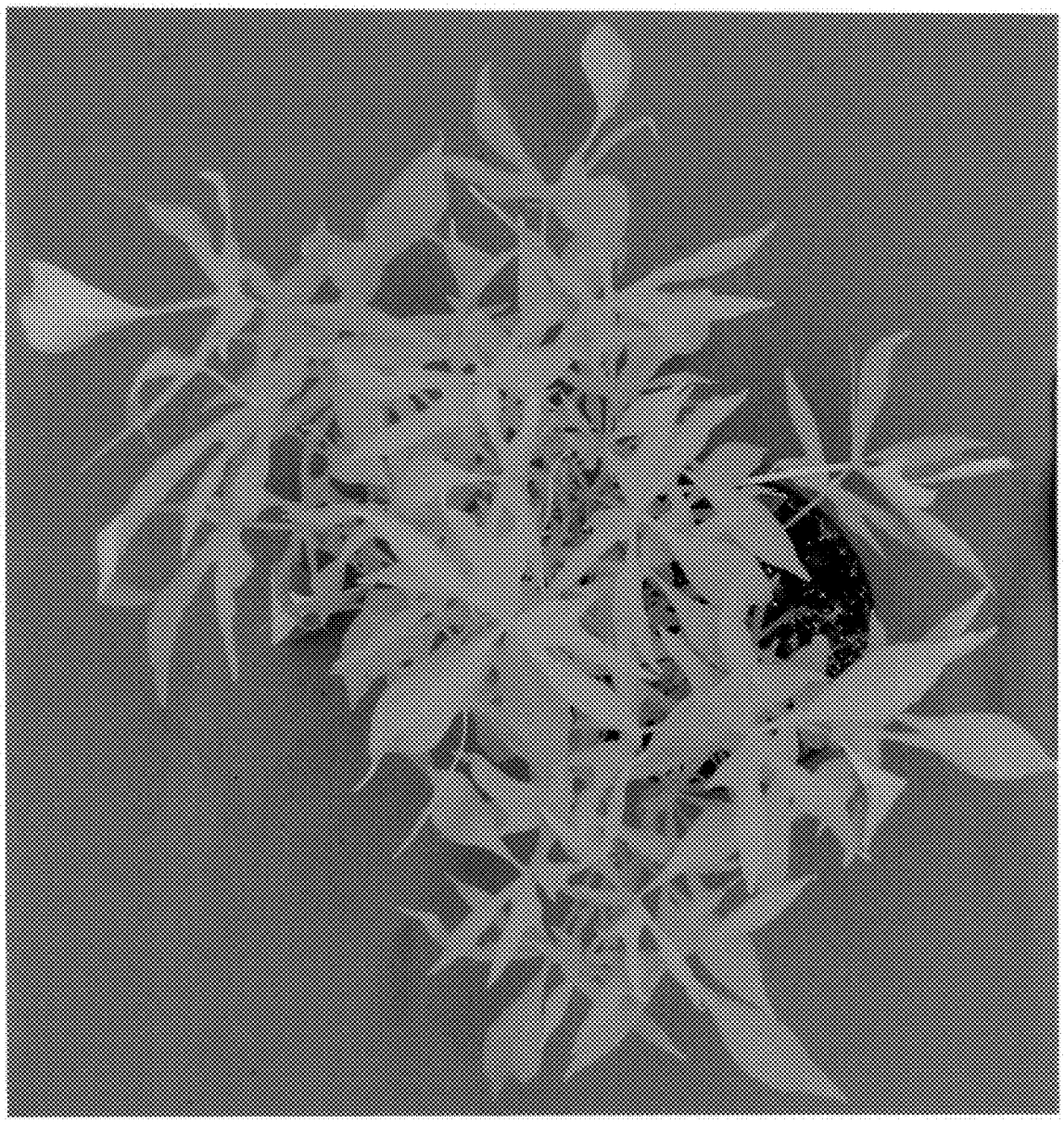
FIG. 2 shows a typical specimen of 'NCORNSP-012EMLC' from the top, 81 days after planting.
Figure 3:
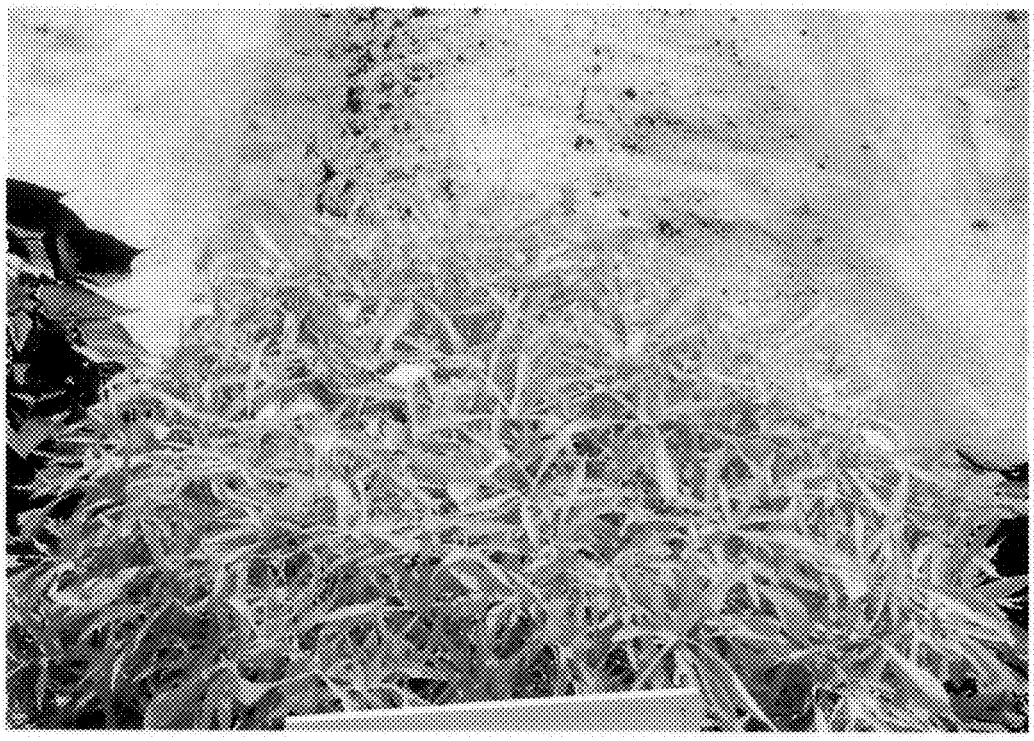
FIG. 3 shows a typical specimen of 'NCORNSP-012EMLC' from the side in the field, 59 days after planting.
Figure 4:
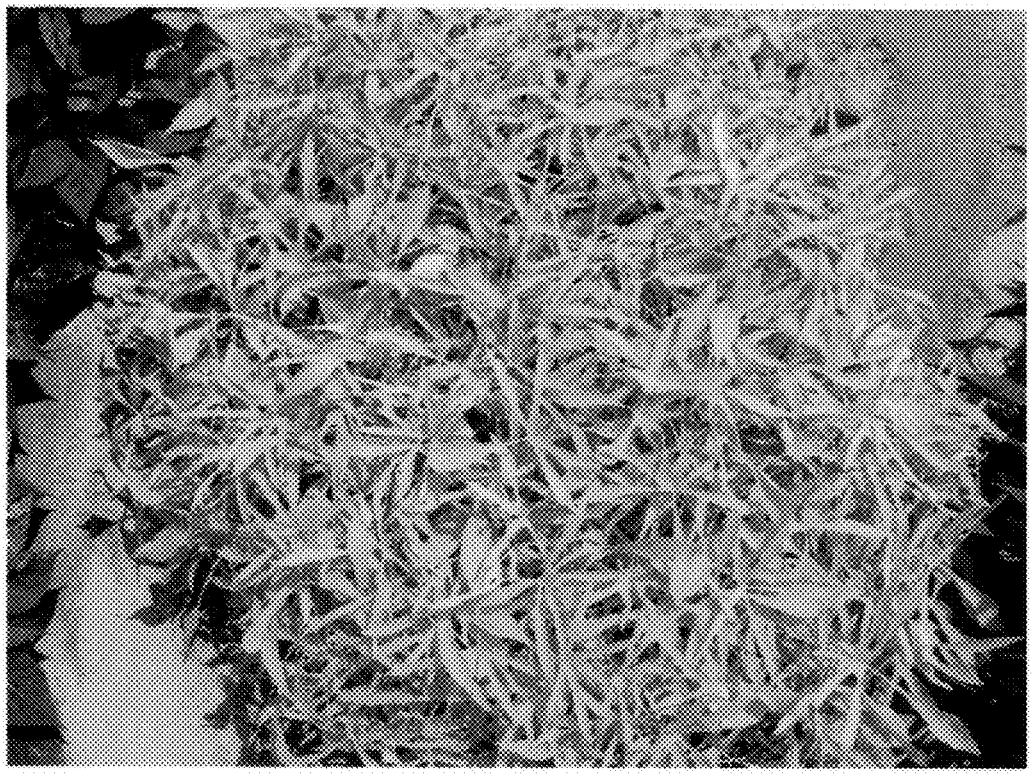
FIG. 4 shows a typical specimen of 'NCORNSP-012EMLC' from the top in the field, 59 days after planting.

Above-ground structure and coloration: FIGS. 1 to 4 show the shape and coloration of a typical specimen of 'NCORNSP-012EMLC'. Colors will vary somewhat due to temperature and nutrient stress. Overall, 'NCORNSP-012EMLC' is a compact, semi-upright, mounded, spreading herbaceous plant that has an average height of 24.8 cm and an average area of spread of 63.5 cm. The growth habit of 'NCORNSP-012EMLC' is to grow upright with shoots growing outward. The foliage is very dense due to many leaves and results in a round uniform plant habit.

Branches:

*Branching habit.*—Freely-branching with about 14 lateral branches coming off the stem. Very dense foliage with no pinching required to stimulate branching. Vegetative lateral shoots: The number of lateral shoots varies, but averages around 6 with multiple short secondary shoots.

*Stem.*—Appearance: Round and glabrous. Aspect: Outward and upward bending. Strength: Very strong. Color: RHS 144B (Bright yellow-green). Length: About 36.2 cm. Diameter: About 1 cm. Internodes: Are short, with an average length of about 1.3 cm; many lateral branches are formed and each axil has latent shoots.

*New shoots.*—Appearance: Glabrous. Aspect: Very slightly undulating. Color: RHS 145B (bright yellow green).

*Vegetative secondary lateral branches.*—Length: About 22.9 cm. Diameter: About 0.5 cm. Internodes: Are short with an average length of about 2.3 cm; many lateral branches are formed and each axil has latent shoots. Color: RHS 145A (bright yellow-green).

*Petiole.*—Length: Varies with an average of 10.1 cm. Diameter: About 0.3 cm. Color: RHS N145B with flush of RHS 59A at point of attachment to leaf.

Foliage (leaves):

*Appearance and arrangement.*—Leaves are alternate, with a matte appearance and tend to spiral around the stem. They are simple and extremely divided into 5 to 7 lobes.

*Shape.*—Broadly to narrowly linear and somewhat variable as is size.

*Quantity.*—About 16 to 18 leaves per lateral branch.

*Mature leaf.*—Length: About 14.0 cm. Width: About 15.5 cm. Lobes: Central Lobe shape: Narrowly oblanceolate. Central Lobe length: About 9.9 cm. Central Lobe width: About 2.6 cm. Mid-vein lobe length: About 7.5 cm. Mid-vein lobe width: About 1.3 cm. Two axillary lobes: Tripartite, one long, linear lobe, one moderate length lobe, and one short lobe; irregular oblanceolate shaped.

*Apex.*—Acuminate.

*Base.*—Cordate.

*Margin.*—Entire.

*Texture upper surface.*—Glabrous.

*Texture lower surface.*—Glabrous.

*Venation pattern.*—Palmate but pinnate with individual lobes.

*Color* (*of mature and immature leaves and venation*).—Table 1 shows that the leaves go from green to purple as they mature.

TABLE 1

Color of Foliage and Venation

| Leaf Structure | Upper Surface | Lower Surface |
|---|---|---|
| Immature Leaf | RHS N144A (Bright green) | RHS N144A (Bright green) |
| Mature Leaf | RHS N144C (Bright green) | RHS N144D (Bright green) |
| Vein-mature leaf | RHS 151A | RHS N144D |
| Vein-immature leaf | RHS 151A | RHS N144D |

Flowers:

*General.*—Flowers rarely occur and if so only under short day conditions. The precise photoperiod for flower induction is currently unknown. When flowering does occur there is some variation in flower size and color depending on the environmental conditions.

*Type and arrangement.*—Solitary, regular funnelform flowers arising from leaf axils on secondary lateral branches are formed.

*Lastingness of flowers on the plant.*—When flowers do occur, they remain open for a period of 4-6 hours, beginning at daybreak dependant on day-length and temperature.

*Fragrance.*—Slight.

*Buds.*—Shape: Elliptic to lanceolate. Width: About 0.6 cm. Length: About 2 cm. Color: RHS 145C, 64D (light lavender, green).

*Corolla.*—General: Composed of 5 fused petals which form a funnel with a pentagonal limb. Width: About 4.9 cm. Length: About 4.3 cm. Throat (tube): Outer throat: RHS 77A (light lavender). Inner throat: RHS 76C (lavender). Petals: Fused to form a funnel shaped corolla with a pentagonal limb. Color, upper surface: RHS 76C (lavender) fading to RHS N155B (light lavender). Color, lower surface: RHS 77A (light lavender) fading to RHS N155B (light lavender).

*Limb color.*—RHS N155B (Light lavender).

*Limb shape.*—Pentagonal.

*Sepals.*—Quantity per flower: 5. General: The two outer sepals are shorter than the three inner sepals. Shape: The sepals are lanceolate and obovate. Apex: Acute. Length: About 1.1 cm. Width: About 0.4 cm. Color: Upper surface: RHS 146C-145B (green). Lower surface: RHS 146C-145B (green).

*Peduncle.*—Color: RHS N77A (light green). Length: 3.2 cm. Diameter: 0.3 cm.

Reproductive organs: Descriptions are based on: CIP, AVRDC, IBPGR. 1991. Descriptors for Sweet Potato. Huaman, Z., editor. International Board for Plant Genetic Resources, Rome, Italy.

*Stigma.*—Color: RHS 155C (white). Placement: Is exerted relative to the stamens. Length: 2.2 cm. Width: 0.1 cm.

*Style color.*—RHS 155C (white).

*Ovary.*—Superior with two locules that contain one or two ovules. At the base of the ovary there are basal glands containing nectar continuing halfway up the ovary. Ovary color: RHS 2C (yellow). Basal gland color: RHS 17A (orange).

*Stamen.*—Quantity per flower: 5. Anther length: About 0.3 cm. Anther color: RHS 155D (cream). Pollen production: sparse. Pollen color: RHS 155D (cream).

Disease or pest resistance: 'NCORNSP-012EMLC' is susceptible to Sweetpotato Feathery Mottle Virus and damage by Japanese beetles. Resistance or susceptibility to other known insects and pathogens of sweetpotato is unknown.

Storage root coloration: Plants form none, to very small, underground storage roots that are highly malformed and do not meet USDA Sweetpotato Storage Root Grade Standards. Storage roots that do form typically possess RHS N77B (Purple) colored skin with hints of RHS 64A (Rose) and RHS 159A (Tan); flesh color is RHS 158B (Cream) with RHS 64A (Purple) spots.

COMPARISON WITH PARENTAL LINE AND KNOWN VARIETIES

Table 2 shows a comparison of 'NCORNSP-012EMLC' with the female parent 'NC2591-002ORN' and the male parent 'NC2279-001ORN' (unpatented).

TABLE 2

| Characteristic | 'NCORNSP-012EMLC' | Female Parent 'NC2591-002ORN' | Male Parent 'NC2279-001ORN' |
|---|---|---|---|
| Plant habit | Compact, semi-upright, mounding | Trailing | Compact |
| Mature leaf color | Bright green | Green | Light green |
| Leaf shape | Very deeply-lobed | Very deeply-lobed | Deeply-lobed |

Table 3 shows a comparison of 'NCORNSP-012EMLC' with 'Sweet Caroline Light Green' (U.S. Plant Pat. No. 15,028) and 'Sweet Caroline Purple' (U.S. Plant Pat. No. 14,912).

TABLE 3

| Characteristic | 'NCORNSP-012EMLC' | 'Sweet Caroline Light Green' | 'Sweet Caroline Purple' |
|---|---|---|---|
| Plant habit | Compact, semi-upright, mounding | Moderately compact | Moderately compact |
| Mature leaf color, upper surface | RHS N144C (Bright green) | Mixture of RHS 151A and RHS 151B (Light green) | RHS 187A (Purple) |
| Leaf size, mature | Length is 14.0 cm and width is 15.5 cm | Length is 12.4 cm and width is 10.5 cm | Length is 9.3 cm and width is 9.2 cm |
| Leaf shape | Very deeply-lobed | Moderately to deeply-lobed | Deeply-lobed |

We claim:

1. A new and distinct cultivar of *Ipomoea batatas* plant named 'NCORNSP-012EMLC', substantially as illustrated and described herein.

* * * * *